United States Patent [19]

Sanders et al.

[11] Patent Number: 4,900,384
[45] Date of Patent: Feb. 13, 1990

[54] METHOD AND APPARATUS FOR MAKING ELASTICIZED CONTAINMENT FLAPS

[75] Inventors: Donald J. Sanders, Menasha; Keith G. Bellin, Green Bay; Karl R. Dehn, Appleton, all of Wis.

[73] Assignee: Kimberly-Clark Corporation, Neenah, Wis.

[21] Appl. No.: 207,358

[22] Filed: Jun. 15, 1988

[51] Int. Cl.$^4$ .............................................. B31D 5/04
[52] U.S. Cl. ................................. 156/204; 156/164; 156/200; 156/227; 156/463; 156/465; 604/358; 604/385.2
[58] Field of Search ............... 156/199, 200, 204, 216, 156/227, 461, 463, 465, 164; 264/285; 604/385.2, 358

[56] References Cited

U.S. PATENT DOCUMENTS

| | | | |
|---|---|---|---|
| 4,050,462 | 9/1977 | Woon et al. | 128/287 |
| 4,326,528 | 4/1982 | Ryan et al. | 128/287 |
| 4,662,877 | 5/1987 | Williams | 604/385 |
| 4,695,278 | 9/1987 | Lawson | 604/385 |
| 4,704,115 | 11/1987 | Buell | 604/385 |
| 4,704,116 | 11/1987 | Enloe | 604/385 |
| 4,822,435 | 4/1989 | Igaue et al. | 156/164 |
| 4,834,740 | 5/1989 | Suzuki et al. | 156/164 X |

Primary Examiner—Michael W. Ball
Assistant Examiner—Michele K. Yoder
Attorney, Agent, or Firm—Paul Yee

[57] ABSTRACT

An apparatus for forming at least one elasticized flap section on a substantially continuous web comprises a web supplying mechanism for delivering a moving, substantially continuous web having first and second, oppositely-facing major surfaces, and having first and second side edges. An elastic supplying mechanism delivers at least one elastic member into contact with the web, and an attaching mechanism secures the elastic member to the web. A first folding mechanism bends the web along a primary foldline located inboard from the first side edge of the web to define at least one primary panel portion of the web. The folding mechanism operably moves the primary panel portion to overlie the first major web surface with the elastic member located between the primary panel portion and the first major web surface. A second folding mechanism bends the web along a flap foldline, which is located substantially inboard from the primary foldline and substantially inboard from the elastic member, to define at least one flap panel portion of the web. The second folding mechanism moves the flap panel portion to overlie the second major surface of the web. A third folding mechanism bends a selected marginal section of the primary panel portion to move the marginal section away from its overlying position relative to the first major web surface.

15 Claims, 4 Drawing Sheets

METHOD AND APPARATUS FOR MAKING ELASTICIZED CONTAINMENT FLAPS

FIELD OF INVENTION

The present invention is related to a method and apparatus for forming a flap section on a web. More particularly, the present invention relates to a method and apparatus for integrally forming at least one elasticized flap section on a substantially unitary, continuous web.

BACKGROUND OF INVENTION

Absorbent articles, such as disposable diapers and incontinence garments, have included elasticized leg bands or leg cuffs. For example, conventional elasticized leg band diaper designs have been shown in U.S. Pat. No. 4,050,462 issued Sept. 27, 1977 to L. Woon et al. and U.S. Pat. No. 4,326,528 issued Apr. 27, 1982 to L. Ryan et al.

Supplemental elastic members have been attached to the inner, bodyside liner layer of an absorbent article. For example, see U.S. Pat. No. 4,662,877 issued May 5, 1987 to F. Williams.

Supplemental elasticized flap members have been incorporated into disposable diapers. For example, U.S. Pat. No. 4,695,278 issued Sept. 22, 1987 describes a disposable diaper having dual cuffs at each side of the diaper. U.S. Pat. No. 4,704,116 issued Nov. 3, 1987 to K. Enloe describes a diaper having elasticized flaps which form side pockets.

U.S. Pat. No. 4,704,115 issued Nov. 3, 1987 to K. Buell describes a disposable waste containment garment having elasticized side flaps. The side flaps provide leakage and guard gutters having closed ends and longitudinally elasticized distal edges.

Conventional designs for absorbent articles have included flap members which are elasticized at their distal edges and which are configured to stand upwardly away from the main body of the article. It has, however, been difficult to efficiently and economically manufacture an absorbent article having the desired elasticized flap members. With one conventional technique, each elasticized flap section is formed as a separate component and is then assembled into the absorbent article. Such a technique, however, may be excessively complicated, can require additional materials for assembling the flap member into the article and may require additional controls to regulate the assembling operation.

To more efficiently form to an elasticized flap in an absorbent article, it has been desirable to form the elasticized flap section from a single, unitary portion of the liner material and to concurrently integrate the elastic member at the desired location in the flap section. Conventional manufacturing techniques, however, have not been sufficiently able to efficiently and economically form the integral elasticized flap section from a unitary layer of web material.

BRIEF DESCRIPTION OF THE INVENTION

The present invention provides a distinctive apparatus for forming at least one elasticized flap section on a substantially continuous web. Generally stated, the apparatus of the invention includes web supplying means for delivering a moving, substantially continuous web having first and second, oppositely-facing major surfaces, and having first and second side edges. Elastic supplying means deliver at least one elastic member into contact with the web, and attaching means secure the elastic member to the web. First folding means bend the web along a primary foldline located inboard from the first side edge of the web to define at least one primary panel portion of the web. The folding means operably moves the primary panel portion to overlie the first major web surface with the elastic member located between the primary panel portion and the first major web surface. Second folding means bend the web along a flap foldline, which is located substantially inboard from the primary foldline and substantially inboard from the elastic member, to define at least one flap panel portion of the web. The second folding means moves the flap panel portion to overlie the second major surface of the web. Third folding means bend a selected marginal section of the primary panel portion to move the marginal section away from its overlying position relative to the first major web surface, thereby forming the elasticized flap section on the web.

The present invention further provides a method for forming at least one elasticized flap section on a substantially continuous web. The method includes the step of delivering a substantially continuous web having first and second, oppositely-facing major surfaces, and having first and second side edges. At least one elastic member is delivered into contact with the web at a selected position, and the elastic member is secured in contact with the web. The web is bent along a primary foldline located inboard from the first side edge of the web to define at least one primary panel portion of the web. The primary panel portion is operably moved to overlie the first major web surface with the elastic member located between the primary portion and the first major web surface. The web is bent along a flap foldline, which is located substantially inboard from the primary foldline and substantially inboard from the elastic member, to define at least one flap panel portion of the web. The flap panel portion is moved to overlie the second major surface of the web. A marginal section of the primary panel portion is bent to move the marginal section away from its overlying position relative to the first major web surface, thereby forming the elasticized flap section on the web.

The distinctive method and apparatus of the present invention can advantageously provide an efficient assembly of the elastic member onto a selected portion of a flexible substrate layer. The invention can reliably reconfigure the unitary layer into a structure having one or more integrally-formed flap sections which extend from the surface of the layer. In addition, the invention can rapidly form the elasticized flap section into the substrate layer during a continuous, inline operation.

BRIEF DESCRIPTION OF THE DRAWINGS

The present invention will be more fully understood and further advantages will become apparent when reference is made to the following detailed description of the invention and the drawings, in which.

BRIEF DESCRIPTION OF THE INVENTION

Figure 1:
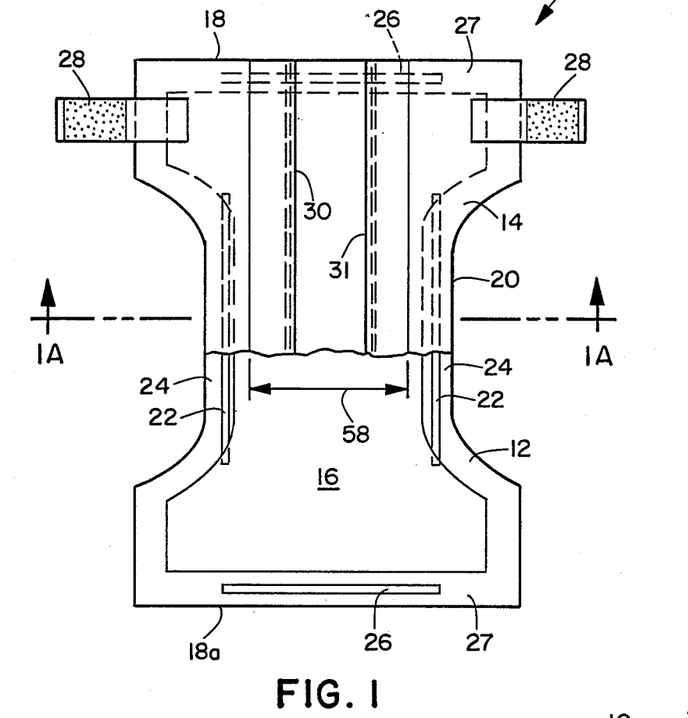
FIG. 1 representatively shows a plan view of a diaper article having a pair of elasticized flap sections.
Figure 1A:
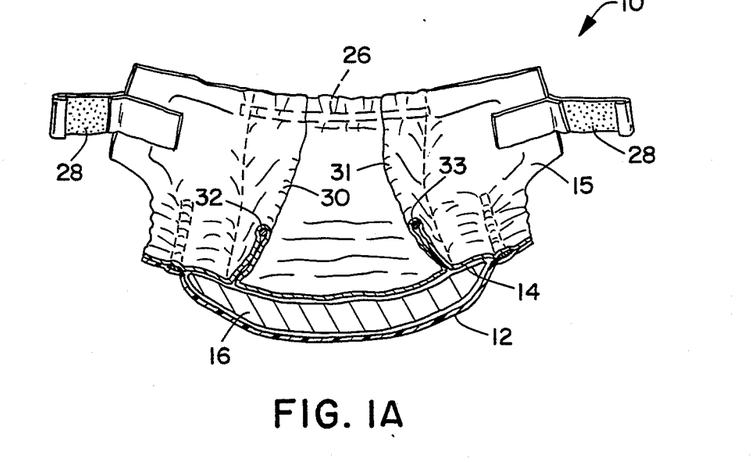
FIG. 1A representatively shows a perspective cross-sectional view taken along line 1A—1A of FIG. 1.

FIGS. 1 and 1A illustrate a representative absorbent disposable diaper article 10 comprising an outer cover layer 12, a bodyside liner layer 14, and an absorbent body 16 sandwiched between the outer cover and bodyside liner layers. Diaper 10 generally defines two waistband sections 18 and 18a interconnected by an intermediate section 20. Outer cover 12 and bodyside line 14 extend out past the lateral side edges of absorbent body 16 to form flexible side margins or leg bands 24 which, during use, are engaged to generally encircle the thighs of the wearer. Leg elastic members 22 are attached to side margins 24 to shir the margins and form flexible elasticized gaskets or cuffs which can more effectively prevent leakage of fluids from the sides of the diaper. Waist elastics 26 are attached to the end margins 27 to form elasticized waistband sections on the diaper. Fastening means such as mechanical-type fasteners or adhesive tape fasteners 28 are connected to opposite sides of the diaper at one longitudinal end thereof, and are employed to secure the diaper about the waist of the wearer.

Outer cover 12 is typically composed of a liquid-impermeable material, such as polyethylene film. Optionally, outer cover 12 may comprise a liquid-impermeable but vapor-permeable material, such as a breathable polymer film or a nonwoven fabric. Bodyside liner 14 is typically composed of a fibrous, nonwoven web, such as a liquid-permeable spunbond web composed of synthetic polymer fibers.

Absorbent body 16 typically comprises an airlaid batt of cellulosic, wood pulp fluff. Optionally, absorbent body 16 may include selected amounts of synthetic polymer fibers and superabsorbent particles. A representative diaper article is described in U.S. Pat. No. 4,699,823 issued Oct. 13, 1987 to S. Kellenberger et al., which is hereby incorporated by reference to the extent that it is consistent with the present disclosure.

To better contain semi-solid body exudates, such as feces, elasticized flap sections 30 and 31 can be arranged to extend from the inner, bodyside surface 15 of liner 14. Elasticized flap sections 30 and 31 includes a flap elastic member 32 connected to the apex, or distal end portion of the flap to operably space the apex of the flap away from the inner surface 15 of the liner, and to form an effective resilient gasketing seal against the buttock region of the wearer. The arrangement and operation of elasticized flap section 30 are described in more detail in U.S. Pat. No. 4,704,116 to K. Enloe, which is hereby incorporated by reference to the extent that it is consistent with the present disclosure.

One technique for forming elasticized flap section 30 has been to preassemble the flap member and its associated flap elastic 32 as a separate subassembly, and then to attach the elasticized flap subassembly to a desired section of bodyside liner 14 with suitable fastening means, such as adhesive, sonic bonds, or the like. A more desirable technique, however, is to form the elasticized flap section as an integral, unitary extension of bodyside line 14. Such a technique can eliminate equipment needed for producing the separate subassembly, transporting the subassembly, precisely positioning the subassembly in the article and securing the subassembly to the bodyside liner.

Figure 2:
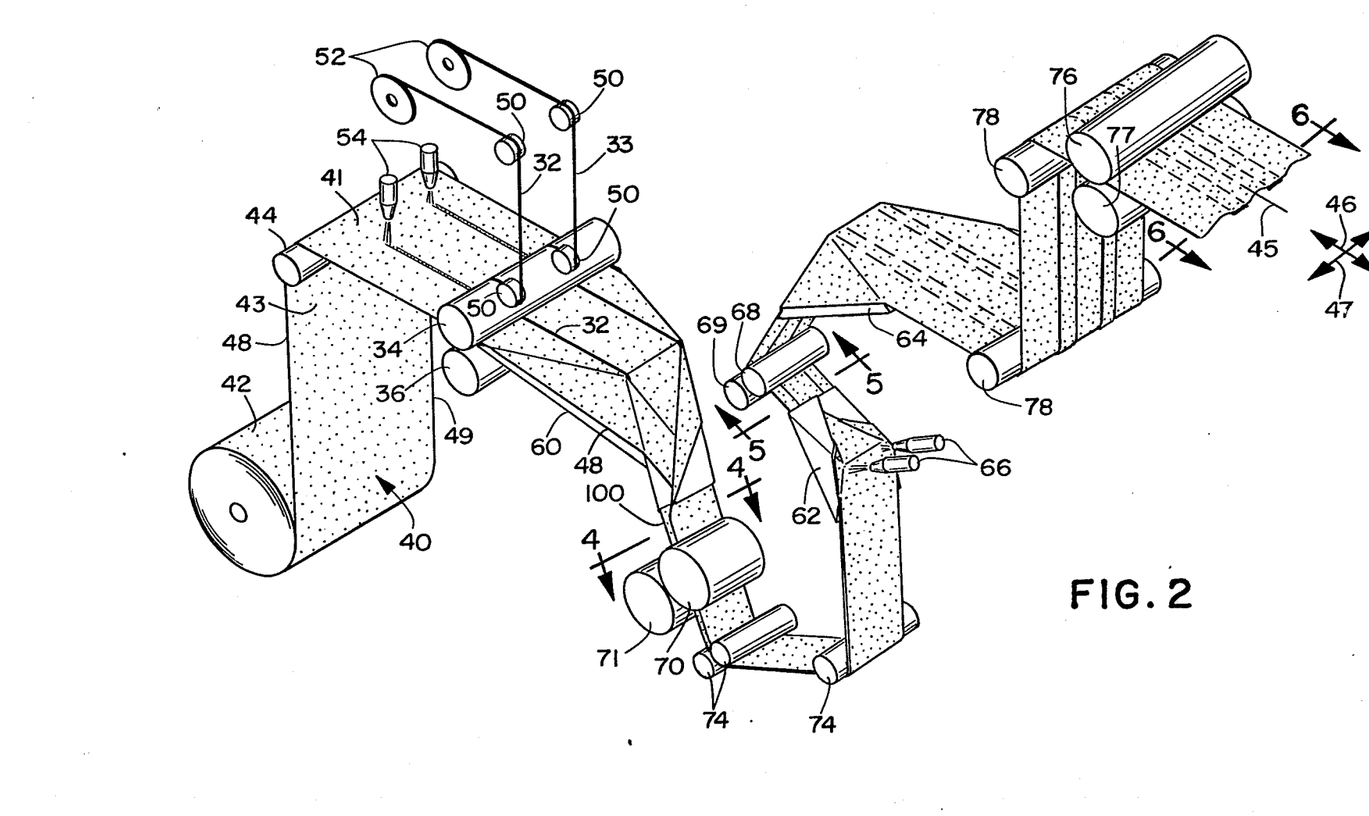
FIG. 2 representatively shows a perspective view of the apparatus of the invention.

Referring to FIG. 2, a web supplying means comprising web supply roll 42 and coveyor roller 44. In the illustrated embodiment, web 40 is composed of the material selected for bodyside liner 14 of a disposable diaper 10 (FIG. 1). The web supplying means delivers a moving, substantially continuous web having first and second oppositely-facing major surfaces 41 and 43, respectively, and having first and second side edges 48 and 49, respectively (FIG. 2).

Figure 4:
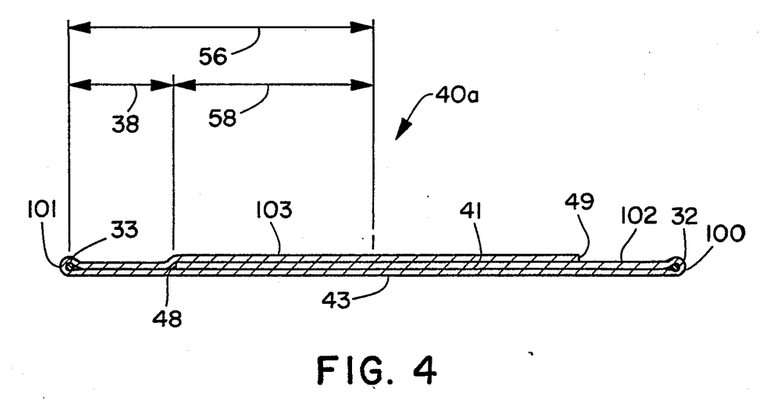
FIG. 4 representatively shows a schematic cross-sectional view of a folded web taken from station 4—4 of FIG. 2.

An elastic supplying means, comprising elastic conveyor rollers 50 and elastic source 52, delivers one or more elastic member 32 into contact with web 40. Attaching means, such as adhesive applicator 54 and elastic applicator rollers 34 and 36, secure elastic member 32 in contact with web 40. A first folding means, such as first folding board 60, bends web 40 along a primary foldline 100, which is located inboard from the first side edge 48 of web 40, to define at least one primary panel portion 102 of the web (FIG. 4). Folding board 60 operably moves the primary panel portion to overlie first major web surface 41 with elastic member 32 located between primary panel portion 102 and first major web surface 41. The resultant primary foldline essentially defines the distal edge elasticized flap. Typically, elastic member 32 is located at the apex line of the elasticized flap section, but may optionally be positioned within the flap section at alternative locations spaced from the apex line.

A second folding means, such as second folding board 62, bends web 40 along a flap foldline 104, which is located substantially inboard from primary foldline 100 and substantially inboard from flap elastic member 32, to define at least one flap panel portion 108 of web 40. The flap panel contains the elastic member therein. Folding board 62 moves the flap panel portion to overlie the second major surface 43 of web 40. The resultant flap foldline essentially defines a line at the base of the elasticized flap.

A third folding means, such as third folding board 64, bends a selected marginal section 110 of primary panel portion 102 to move the marginal section away from its overlying position relative to first major web surface 41, thereby forming an elasticized flap section 30 on web 40.

In a particular aspect of the invention, the method and apparatus can be distinctively configured to form a plurality of flap sections 30 on web 40. For example, the invention can be configured to form a pair of elasticized flap sections 30, 31 which extend longitudinally along the machine direction 46 or web 40. Preferably, the pair of elasticized flap sections 30 and 31 are substantially equally spaced from a longitudinal centerline 45 of web 40, although unequal spacing may also be employed, if desired.

To form a complimentary pair of elasticized flap sections 30, 31, the various mechanisms of the present invention can be configured with a substantially bilateral symmetry about the centerline of web 40. The required mechanisms and process steps that are associated with forming a first elasticized flap section at one side of centerline 45 can be substantially duplicated to form a second elasticized flap section 31 on the other, laterally opposite side of the centerline. The following description will be made in the context of a device for forming a complimentary pair of elasticized flap sections. It will, however, be readily apparent that a single elasticized flap section could be formed with a device which comprises essentially one lateral half of the described apparatus.

The illustrated embodiment of the invention representatively shown in FIG. 2 has a configuration wherein the elastic supplying means delivers a first elastic member into contact with web 40 at a position inboard from first side edge 48 and delivers a second elastic member 33 into contact with the web at a position inboard from second side edge 49. The attaching means then secures the first and second elastic members into contact with the web.

As illustrated in FIG. 4, first folding board 60 bends web 40 along a first primary foldline 100, which is located inboard from web side edge 48, to define a first primary panel portion 102. Folding board 60 also bends web 40 along a second primary foldline 101, which is located inboard from web side edge 49, to define a second primary panel portion 103 of the web. Folding board 60 operably moves the first and second primary panel portions 102, 103 to overlie the first major web surface 41. As a result, elastic member 32 becomes located between primary panel portion 102 and web surface 41, and second elastic member 33 becomes located between primary panel portion 103 and web surface 41. The resultant, complementary pair of primary foldlines essentially define the distal edges of elasticized flap sections 30 and 31, and form an elasticized apex line on each of the elasticized flaps. In the shown embodiment, the distal edges extend in a generally parallel configuration along the machine direction of web 40.

Figure 5:
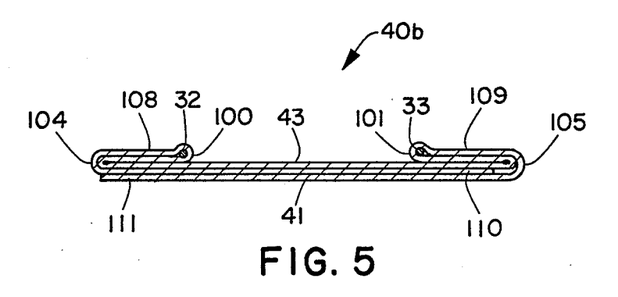
FIG. 5 representatively shows a schematic cross-sectional view of a folded web taken from station 5—5 of FIG. 2.

As representatively shown in FIG. 5, second folding board 62 then bends the web along a first flap foldline 104, which is located inboard from primary foldline 100 and inboard from first elastic member 32, to define a first flap panel portion 108 of the web. Folding board 62 also bends web 40 along a second flap foldline 105, which is located inboard from primarily foldline 101 and inboard from second elastic member 33, to define a second flap panel portion 109 of the web. Folding board 62 moves the first and second flap panel portions to generally overlie second major surface 43 of web 40. The resultant, complementary pair of flap foldlines essentially define a line at the base of each of the elasticized flap sections. In the shown configuration, the two base lines extend in a generally parallel arrangement along the machine direction of web 40.

Figure 6:
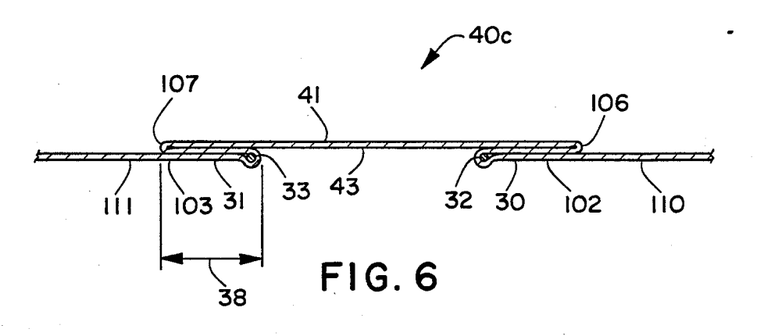
FIG. 6 representatively shows a schematic cross-sectional view of a folded web taken at station 6—6 of FIG. 2.

With reference to FIG. 6, third folding board 64 bends a marginal section 110 of first primary panel 102 and bends a marginal section 111 of second primary panel 103 to move the marginal sections away from their overlying positions relative to first major web surface 41, thereby forming a pair of elasticized flap sections 30, 31 on the web. The elasticized flap sections lie bent over sideways against a medial portion of web 40 in a storage position.

Referring again to FIG. 2, the elastic supplying means may comprise a conventional mechanism for delivering elastic strands from one or more prepared spools. Alternatively, the elastic strands may be provided by a conventional mechanism which extrudes continuous threads or ribbons of synthetic elastic polymer in line with the manufacturing operation.

In the shown embodiment of the invention, elastic members 32, 33 move from a suitable elastic supply source 52 and are directed by conveyor rollers 50 to applicator roll 34. The elastic members travel around applicator roll 34 and are pressed into contact with web 40 at the nip between applicator roll 34 and an associated, counter-rotating web support roll 36.

Adhesive applicator 54 comprises a mechanism for applying an operable amount of adhesive to the elastic members. For example, the adhesive applicator may extrude a layer of adhesive onto the elastic member or onto web 40. Also alternatively, the adhesive applicator may subject the elastic member to a bath of adhesive prior to placing the elastic member in contact with the web. In the illustrated embodiment, adhesive applicator 54 applies a pair of spray patterns of adhesive onto web 40. Each of the spray patterns is generally centered about the desired location of its associated flap elastic member on the web. In addition, the cross-directional width of each spray pattern is approximately equal 1–2 times the desired height 38 (FIG. 6) of the elastic flap section. As the individual flap elastic members are brought into contact with web 40, the elastic members operably engage the previously applied patterns of adhesive. In the nip between rolls 34 and 36, the elastic strands become pressed against the adhesive and become operably bonded to the web. While the illustrated embodiment of the invention includes a single strand of elastic in each flap section, alternative embodiments of the invention may optionally include multiple elastic strands in each flap section.

Elastic conveyor rollers 50 are suitably arranged to guide the individual elastic members 32 and 33 into a selected spacing from the web centerline 45 along the cross-direction 47 of web 40. The cross-directional spacing 56 of the elastics (FIG. 4) approximately equals one flap height 38 plus one flap spacing 58.

Figure 3:
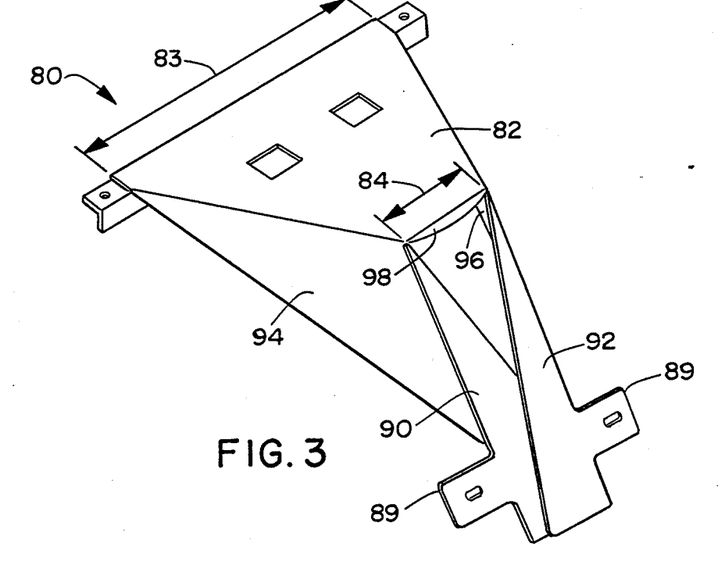
FIG. 3 representatively shows a perspective view of a typical folding board assembly employed with the present invention.
Figure 3A:
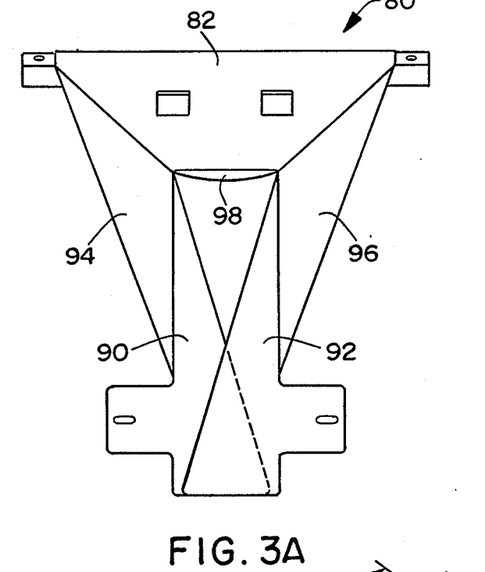
FIG. 3A representatively shows a front elevational view of the folding board assembly.
Figure 3B:
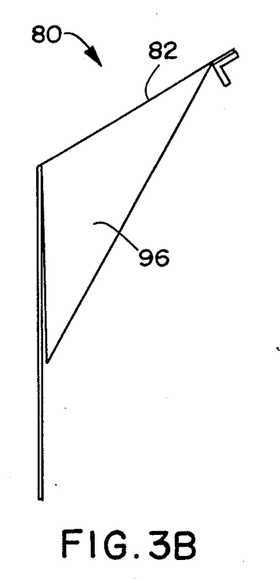
FIG. 3B representatively shows a side elevational view of the folding board assembly.

FIGS. 3, 3A and 3B representatively shows a typical folding board 80 employed with the present invention. The folding board includes a table portion 82, side skirts 94 and 96, and front skirt 98. In addition, the folding board includes complimentary folding blades 90 and 92, which are located at each side of table 82.

In the illustrated embodiment, table 82 is generally trapezoidal in shape with an overall width dimension 83 which is sufficient to operably support web 40. Table 82 tapers down to a root section which has a root dimension 84 that essentially corresponds to the desired cross-directional spacing between the selected foldlines formed in web 40. For example, with respect to first folding board 60, root dimension 84 corresponds to the desired cross-directional spacing between primary foldlines 100 and 101 (FIG. 4). With respect to second folding board 62, root dimension 84 essentially corresponds to the desired cross-directional spacing between flap foldlines 104 and 105 (FIG. 5). Similarly, with respect to third folding board 64, root dimension 84 essentially corresponds to the desired cross-directional spacing between unfoldlines 106 and 107 (FIG. 6).

Folding board 80 further includes a complimentary pair of folding blades 90 and 92. The folding blades are generally triangular in shape, and one folding blade is positioned at each end of root dimension 84 with one apex of each triangle in operable engagement with table 82. Each folding blade is constructed and arranged in a conventional manner that is well known in the art to engage one marginal edge of the web, and to operably direct and traverse the edge of the web over the medial section of the web and toward the web centerline.

Table 82 further includes a pair of side skirts 94 and 96, and a front skirt 98. With the illustrated embodiment, the side skirts are angled downwardly at an operative acute angle with respect to a phantom extension of the plane defined by table 82. The operable angles are readily determined by persons skilled in the art of conventional folding boards. For example, the angle between the underside of table 82 and side skirts 94 and 96 may be about 106°. Similarly, front skirt 98 is angled downwardly by an operative acute angle from a hypothetical, phantom continuation of the plane generally defined by table 82. For example, the angle between front skirt 98 and the plane defined generally by table 82 may be about 39°.

The plane defined by folding blade 90 is angled downwardly and approximately along the plane of front skirt 98, with the outboard, side edge of the triangular blade operably providing a continuation of side skirt 94. Similarly, folding blade 92 is angled generally along the plane of front skirt 98 with one side edge of the blade operably providing a continuation of side skirt 96.

The geometric planes defined by folding blades 90 and 92 can be slightly skewed with respect to each other to allow the blades to overlap, as representatively shown in FIGS. 3 and 3A. This arrangement permits the formation of a folded configuration of web 40 wherein the primary panel portions 102 and 103 overlap the medial section of web 40 and also overlap each other by a discrete amount. Each folding blade includes a mounting flange 89 for securing the folding blade to a suitable support mechanism that operably holds the folding blade in proper position and orientation during use.

When the folding board is in operation, web 40 is drawn over table 82, and the medial portion of the web over front skirt 98. At the region where a folding blade approximately intersects the root dimension of table 82, a pinch-tuck is formed in the web to initiate the corresponding foldline in the web. Concurrently, the side marginal portions of the web are drawn down and over the side skirts 94 and 96. Upon leaving the side skirts, the marginal portions of the web contact the corresponding adjacently located side edges of folding blades 90 and 92, and then transverse over the folding blades toward the inboard edges thereof. As the marginal portions of the web move over the folding blades, the marginal edges of the web are translated toward the web centerline to form the folded panel in the web.

When the folding board is configured into an unfolding mode of operation, the above described sequence of events is essentially reversed. More particularly, the overlying marginal edges of the web first contact the inboard edges of the folding blades, and are then drawn over the folding blades toward the outboard edges thereof. This translates the web edges away from the web centerline. The marginal portions of the web that transverse over the folding blades then move over the side skirts and the table of the folding board. Concurrently, the folded edges of the web moves into the regions where the folding blades intersect the ends of the root dimension of table 82, and become unfolded.

In the present invention, the first, second and third folding boards 60, 62 and 64, respectively, are similarly configured. The folding boards differ slightly in dimensional size depending upon the desired locations at which the particular folding board is configured to produce folds or unfolds in web 40. The differences between the individual folding boards will be described in more detail below.

Referring again to FIG. 2, web 40 moves over folding board 60 after the elastic members have been suitably placed in contact with the web. During the operation of folding board 60, the ends of the root dimension of table 82 cooperate with the associated apexes of folding blades 90 and 92 to form a tuck which initiates the bending of the web to form foldlines 100 and 101, respectively. In the illustrated embodiment, the primary foldlines are formed at the approximate location of elastic members 32 and 33 such that primary panel portions 102 and 103 bend over the elastic members and sandwich the elastic members between the medial section of web 40 and the associated, primary panel sections of the web (FIG. 4).

Side skirts 94 and 96 direct the lateral side portions of web 40 thereover to form primary panels 102 and 103, respectively. The side skirts also direct the primary panel portions into an overlying relation with respect to major surface 41 of web 40. A representative cross-sectional view of folded web 40a after it has been processed and rearranged by folding board 60 is illustrated in FIG. 4.

After web 40 has been folded by folding board 60, the web passes into the nip between bonding rollers 70 and 71. The bonding rollers urge the folded sections of web 40 into intimate contact with each other and with elastic members 32 and 33, which have been sandwiched within the folded web. The adhesive previously applied to web 40 by applicator 54 bonds at least a portion of the overlying web panel portions to major surface 41 of the web. In a particular embodiment of the invention, the folded over and bonded portion has a cross-directional width which substantially corresponds to the desired elasticized flap height 38.

Conveyor rollers 74 direct web 40 to a second folding board 62. The folding board is constructed and arranged with a folding table having a root dimension which is substantially equal to the desired cross-directional flap spacing 58 on diaper 10. Accordingly, with the shown embodiment of the invention, the flap height 38 of elasticized flap sections 30 and 31 can be represented by the equation:

$$h = (r_1 - r_2)/2$$

where:
h = flap height
$r_1$ = root dimension of first folding board
$r_2$ = root dimension of second folding board Second folding board 62 is constructed and arranged to bend web 40 about first and second flap foldlines 104 and 105, respectively. Flap foldline 104 is located inboard from the first primary foldline 100 and also inboard from the first elastic member 32. Similarly, flap foldline 105 is positioned inboard from the second primary foldline 101 and inboard from the second elastic member 33. As a result, the bending of the web about the first and second flap foldlines 104 and 105 defines a first flap panel 108 and a second flap panel 109, respectively. Each of the flap panels includes an elastic member assembled thereto. In relative contrast to folding board 60, second folding board 62 folds the web in the opposite direction. As a result, the folded flap panels 108 and 109 generally overlie the second major surface 43 of web 40. FIG. 5 representatively shows a cross-sectional view of folded web 40b after it has been creased and folded by second folding board 62.

Referring again to FIG. 2, associated end-seal adhesive applicators 66 are positioned over folding board 62. Adhesive applicators 66 intermittently apply adhesive to the second major surface 43 of web 40a prior to the actual folding of the web along flap foldlines 104 and 105. The adhesive is selectively placed and registered with those sections of web 40 that will comprise the end margins 27 of the final, assembled diaper 10. The end margins of the diaper, where the bodyside liner overlies and is adhered to the outer cover, are commonly referred to as the end-seal regions of the diaper. As a result of the subsequent folding operation provided by second folding board 62, spaced sections of flap panels 108 and 109 become bonded to surface 43 of web 40. The bonded sections of the flap panels are spaced at predetermined intervals along the machine direction 46 of the web, and the end-seal adhesive provided by applicators 66 holds the elasticized flap sections 30 and 31 flat against the main body of the diaper at the diaper waistband sections. The adhesive bond substantially prevents the waistband portions of the elasticized flap sections from rising up away from the general plane of the diaper under the tensioning influence of elastic members 32 and 33.

After the folding operation provided by folding board 62, folded web 40b moves into the nip between bonding rollers 68 and 69. The bonding rollers press flap panels 108 and 109 against web surface 43 to assure an adequate, firm bond by the end-seal adhesive.

Upon leaving bonding nip rollers 68 and 69, web 40b moves to third folding board 64, which actually is arranged to perform an unfolding operation. Folding board 64 is arranged and positioned in a reverse configuration such that web 40b contacts the side blades and side skirts of the folding board. As a result, folding board 64 bends marginal sections 110 and 111 of the primary panel portions 102 and 103 to operably move the marginal sections away from their previous overlying positions relative to web major surface 41. In the shown embodiment of the invention, folding board 64 has a root dimension which is substantially equal to the root dimension of first folding board 60. As a result, first and second unfoldlines 106 and 107 substantially correspond to the locations of primary foldlines 100 and 101, respectively. Thusly configured, unfoldlines 106 and 107 are effectively positioned at the base of elasticized flap sections 30 and 31, respectively. FIG. 6 illustrates a representative cross-sectional view of folded web 40c after it has been reconfigured and unfolded by third folding board 64.

After processing by folding board 64, conveyor rollers 78 move web 40c to a mechanism which selectively removes or otherwise avoids the occurrence of elastic contractibility at selected portions of the elasticized section. The illustrated embodiment of the invention, for example, a heated roller assembly comprising a pair of nipping rollers 76 and 77. The nipping rollers are constructed and arranged to heat predetermined selected regions of flap elastic members 32 and 33 to substantially destroy the elastic contractibility in those sections that correspond to the waistband end-seal regions of diaper 10. For example, a conventional timing mechanism can be employed to coordinate the operation of heating rollers 76 and 77 with the operation of adhesive applicators 66. The coordination is such that the heating rollers selectively remove or "kill" the elastic contractibility of elastic members 32 and 33 in those portions of elasticized flap sections 30 and 31 that have been bonded and adhered against major surface 43 of web 40.

In an alternative embodiment of the invention, the means for removing the elastic contractibility from selected portions of the elasticized flap sections may comprise a mechanism which physically removes the elastic material from the appointed waistband portions of the elasticized flap sections. For example, elasticized flap sections 30 and 31 may be constructed such that upon cutting of web 40 at its appointed end-seal sections, certain limited regions of the corresponding sections of flap elastic members 32 and 33 are able to operably retract away from the end-seal sections. In still another embodiment of the invention, the means for removing the elastic contractibility from portions of the flap sections may comprise a mechanism which operably cuts or otherwise separates appointed portions of the elastic material into pieces. The pieces are small enough to effectively remove the elasticity from the end-seal regions of the flap sections.

Having thus described the invention in rather full detail, it will be readily apparent that various changes and modifications may be made. All of such changes and modifications are contemplating as being within the scope of the invention, as defined by the subjoined claims.

We claim:

1. An apparatus for forming at least one elasticized flap section on a substantially continuous web, comprising:
    web supplying means for delivering a moving, substantially continuous web having first and second, oppositely facing major surfaces, and having first and second side edges;
    elastic supplying means for delivering at least one elastic member into contact with said web;
    attaching means for securing said elastic member to said web;
    first folding means for bending said web along a primary foldline located inboard from said side edge of said web to define at least one primary panel portion of said web, thereby operably moving said primary panel portion to overlie said first major web surface with said elastic member located between said primary panel portion and said first major web surface;
    second folding means for bending said web along a flap foldline located substantially inboard from said primary foldline and substantially inboard from said elastic member to define at least one flap panel portion of said web, and for moving said flap panel portion to overlie said second major surface of said web; and
    third folding means for bending a selected marginal section of said primary panel portion to move said marginal section away from its overlying position to said first major web surface, thereby forming said elasticized flap section on said web.

2. An apparatus as recited in claim 1, further comprising attaching means for securing predetermined, limited sections of said folded, elasticized flap section onto said web.

3. An apparatus as recited in claim 1, further comprising means for substantially avoiding elastic contractibility at selected portions of said elasticized flap section.

4. An apparatus as recited in claim 1, wherein said elastic supplying means delivers a first elastic member into contact with said web at a position inboard from said first side edge, and delivers a second elastic member into contact with said web at a position inboard from said second side edge;

said attaching means secures said first and second elastic members into contact with said web;

said first folding means bends said web along a first primary foldline located inboard from said first side edge of the web to define a first primary panel portion, and bends said web along a second primary foldline located inboard from said second side edge of the web to define a second primary panel of the web, thereby operably moving said first and second primary panel portions to overlie said first major web surface, with said first elastic member located between said first primary panel portion and said first major web surface, and with said second elastic member located between said second primary panel portion and said first major web surface;

said second folding means bends said web along a first flap foldline, which is located inboard from said first primary foldline and inboard from said first elastic member, to define a first flap panel portion of the web, and bends said web along a second flap foldline, which is located inboard from said second primary foldline and inboard from said second elastic member, to define a second flap panel portion of the web, thereby moving said first and second flap panel portions to generally overlie said second major surface of the web; and said third folding means bends a marginal section of said first primary panel portion and bends a marginal section of said second primary panel portion to move said marginal sections away from their overlying positions relative to said first major web surface, thereby forming a pair of elasticized flap sections on said web.

5. An apparatus as recited in claim 4, further comprising attaching means for securing predetermined, limited sections of said folded, elasticized flap section onto said web.

6. An apparatus as recited in claim 4, further comprising means for substantially avoiding elastic contractibility at selected portions of said elasticized flap section.

7. An apparatus as recited in claim 4, wherein said third folding means bends said marginal section of said first primary panel portion substantially along said first flap foldline, and bends said marginal section of said second primary panel portion substantially along said second flap foldline.

8. A method for forming at least one elasticized flap section on a substantially continuous web, comprising the steps of:
 a. delivering a substantially continuous web having first and second oppositely facing major surfaces, and having first and second side edges;
 b. delivering at least one elastic member into contact with said web at a selected position;
 c. securing said elastic member in contact with said web;
 d. bending said web along a primary foldline located inboard from said first side edge of said web to define at least one primary panel portion of said web, and operably moving said primary panel portion to overlie said first major web surface with said elastic member located between said primary panel portion and said first major web surface;
 e. bending said web along a flap foldline, which is located substantially inboard from said primary foldline and substantially inboard from said elastic member, to define at least one flap panel portion of said web, and moving said flap panel portion to overlie said second major surface of said web;
 f. bending a marginal section of said primary panel portion to move said marginal section away from its overlying position relative to said first major web surface, thereby forming said elasticized flap section on said web.

9. A method as recited in claim 8, wherein said step of bending said marginal section of said primary panel portion comprises the step of bending said marginal section along a folding line which substantially corresponds to said flap foldline.

10. A method as recited in claim 8, further comprising the step of securing predetermined, limited sections of said folded, elasticized flap section onto said web.

11. A method as recited in claim 8, further comprising the step of substantially avoiding elastic contractibility at selected portions of said elasticized flap section.

12. A method for forming at least one pair of elasticized flap sections on a substantially continuous web, comprising the steps of:
 a. delivering a substantially continuous web having first and second oppositely facing major surfaces, and having first and second side edges;
 b. delivering a first elastic member into contact with said web at a position inboard from said first side edges, and delivering a second elastic member into contact with said web at a position inboard from said elastic side edge;
 c. securing said first and second elastic members in contact with said web;
 d. bending said web along a first primary foldline located inboard from said first side edge of the web to define a first primary panel portion of the web;
 e. bending said web along a primary foldline located inboard from said second side edge of the web to define a second primary panel portion of the web;
 f. moving said first and second primary panel portions of the web to overlie said first major web surface, with said first elastic member located between said first primary panel portion and said first major web surface, and with said second elastic member located between said second primary panel portion and said first major web surface;
 g. bending said web along a first flap foldline, which is located inboard from said first primary foldline and inboard from said first elastic member, to define a first flap panel portion of the web;
 h. bending said web along a second flap foldline, which is located inboard from said second primary foldline and inboard from said second elastic member, to define a second flap panel portion of the web;
 i. moving said first and second flap panel portions to generally overlie said second major surface of the web; and
 j. bending a marginal section of said first primary panel portion and bending a marginal section of said second primary panel portion to move said marginal sections away from their overlying positions relative to said first major web surface, thereby forming a pair of elasticized flap sections on said web.

13. A method as recited in claim 12, further comprising the step of securing predetermined, limited sections of said folded, elasticized flap sections onto said web.

14. A method as recited in claim 12, further comprising the step of substantially avoiding elastic contractibility at selected portions of said elasticized flap sections.

15. A method as recited in claim 12, wherein said bending step (j) comprises the step of bending said marginal sections of said first and second primary panel portions along folding lines which substantially correspond to said first and second primary foldlines.

* * * * *